United States Patent [19]

Leonard

[11] 4,264,306
[45] Apr. 28, 1981

[54] DENTAL HAND PIECE
[75] Inventor: Henri Leonard, Besancon, France
[73] Assignee: Micro - Mega S.A., France
[21] Appl. No.: 67,892
[22] Filed: Aug. 20, 1979
[30] Foreign Application Priority Data Aug. 24, 1978 [FR] France .................. 78 24973

[51] Int. Cl.³ .............................. A61C 1/08
[52] U.S. Cl. ................... 433/126; 433/114
[58] Field of Search ............... 433/114, 115, 116, 117, 433/118, 120, 122, 124, 125, 126, 127, 128, 129, 133

[56] References Cited
U.S. PATENT DOCUMENTS

| | | | |
|---|---|---|---|
| 887,388 | 5/1908 | Golly | 433/120 |
| 2,025,779 | 12/1935 | Roelke | 433/133 |
| 2,690,012 | 9/1954 | Kaltenbach | 433/128 |
| 2,879,594 | 3/1959 | Massen | 433/114 |

*Primary Examiner*—Gene Mancene
*Assistant Examiner*—John J. Wilson
*Attorney, Agent, or Firm*—Robert E. Burns; Emmanuel J. Lobato; Bruce L. Adams

[57] ABSTRACT

This dental hand piece, notably of the contra-angle type, comprises three sleeve-like members assembled to each other by screwing and an external socket covering these three sleeves so as to clamp them between an inner shoulder formed at the front end of the socket and the front end of a complementary end sleeve fitted on the rear sleeve and to which the external socket is screwed at its rear end.

4 Claims, 1 Drawing Figure

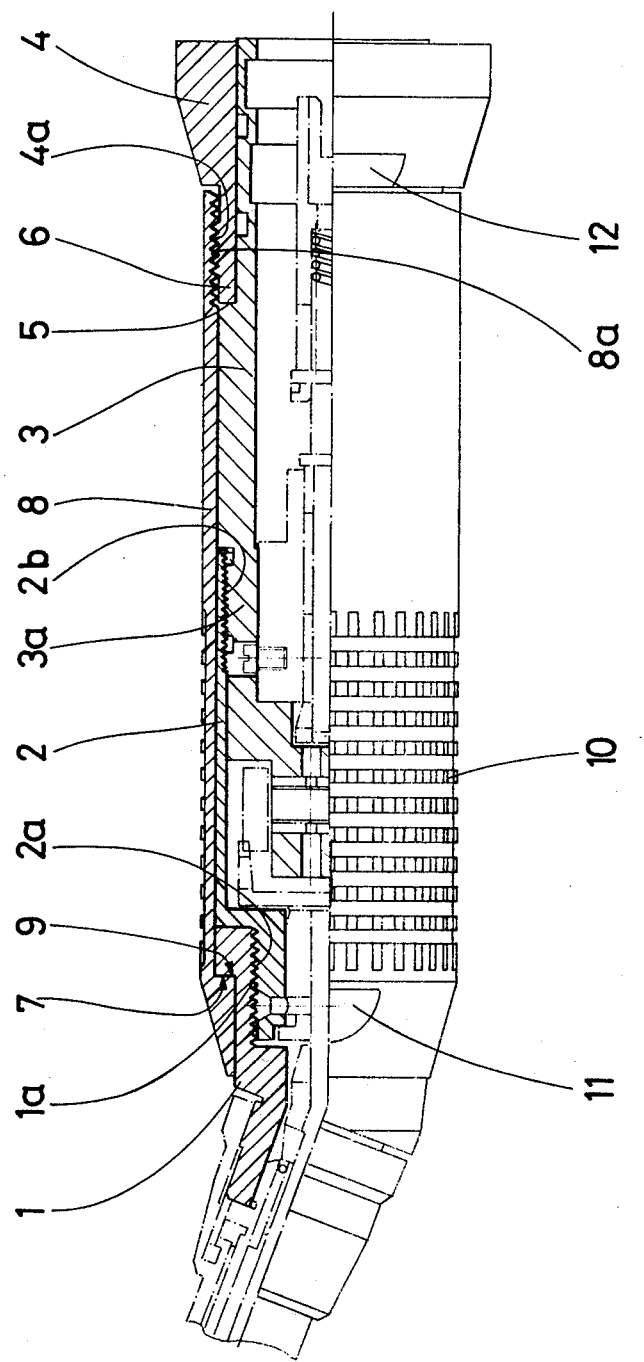

DENTAL HAND PIECE

FIELD OF THE INVENTION

This invention relates to dental hand pieces of the type comprising a bent front sleeve adapted to be screwed on an intermediate straight sleeve screwed in turn on a rear straight handle.

REFERENCE TO THE PRIOR ART

Dental hand pieces and more particularly contra-angles comprises several elements assembled by screwing to one another. When using these hand pieces, for instance when milling a tooth with a bur of relatively large diameter to which a particularly heavy stress is applied, it happens sometimes that the three elements become loose from each other since they are tightened only manually, the use of spanners being precluded due to the reduced wall thickness of the various sleeves.

SUMMARY OF THE INVENTION

It is the primary object of the present invention to avoid this inconvenience. For this purpose, the hand piece according to this invention is characterised in that it comprises an elongated external socket covering the three sleeves and adapted to clamp them between an internal shoulder formed at the front end of said external socket and the front end of a complementary end sleeve mounted on the rear sleeve and to which said socket is screwed at its rear end.

Thus, the three sleeves are safely clamped inside the external socket and this socket further acts as a means for efficiently protecting these component elements.

The invention will now be described with reference to the single FIGURE of the attached drawing illustrating diagrammatically in half axial section and by way of example of typical form of embodiment of a contra-angle constructed according to the teachings of this invention.

DESCRIPTION OF THE PREFERRED EMBODIMENT

The dental hand piece illustrated in the drawing comprises a bent front sleeve 1 directed towards the head of the hand piece and adapted to be screwed by means of its internally threaded rear portion 1a to the front screw-threaded portion 2a of a straight intermediate sleeve 2 screwed in turn at its rear internally threaded end 2b to a straight rear sleeve 3. The drive means known per se, which are no part of the invention, are shown only diagrammatically in dash and dot lines.

The rear sleeve 3 is provided on the one hand at its front end with a screw-threaded portion 3a engaged by the internally screw-threaded portion 2b of the intermediate sleeve 2, and on the other hand in the vicinity of its rear end with an external shoulder 5. A tapered complementary end sleeve 4 is fitted to the rear end of the rear sleeve 3 so that its front end 6 abutes the shoulder 5 of said rear sleeve 3. On the other hand, this front end 6 of the end sleeve 4 is provided with an external threaded portion 4a for a purpose to be explained presently.

The rear end of the front bent sleeve 1 comprises an external shoulder 7.

The three sleeves 1, 2 and 3 are so designed that when screwed home into each other their outer peripheral surfaces are level with each other.

An external elongated socket 8 having an inner bore of a diameter slightly greater than the outer diameter of the three sleeves 1, 2 and 3 is mounted on the assembly comprising these three sleeves so as to cover and protect them. The outer socket 8 has formed at its front end an inner shoulder 9 engaging the outer shoulder 7 of the bent sleeve 1 and at its rear end an internal screw-threaded portion 8a engaging the outer screw-threaded portion 4a of the complementary end sleeve 4.

Thus, when the outer socket 8 fitted on the three-sleeve assembly 1,2 and 3 is screwed to the end sleeve 4, it is clamped tightly between the inner shoulder 9 of outer socket 8 and the front end 6 of the complementary sleeve 4, so that any risk of untimely loosening of the screwed elements is positively prevented.

On the other hand, the outer socket 8 has ribs and grooves 10 formed on its outer surface to facilitate the gripping thereof, together with at least a pair of diametrally opposed flat faces 11 so that a spanner can easily be used for tightening the parts, another pair of opposed flat faces 12 being also provided for this purpose on the complementary end sleeve 4.

What is claimed is:

1. A dental hand piece comprising a rear straight sleeve an intermediate straight sleeve screwed to said rear sleeve, a bent sleeve screwed to said intermediate sleeve, a complementary end sleeve fitted on said rear sleeve, and an elongated external socket which covers the assembly of said front, intermediate and rear sleeves and clamps them tightly between an inner shoulder formed on the front portion of said external socket and the front end of said complementary end sleeve to which said external socket is screwed at its rear end.

2. A dental hand piece according to claim 1, wherein said bent front sleeve is provided at its rear end with an inner shoulder engageable by the inner shoulder of said external socket, said rear sleeve being formed with an outer shoulder engageable by the front end of said complementary end sleeve.

3. A dental hand piece according to claim 1, wherein said external socket and said complementary end sleeve are each provided with at least two diametrally opposed flat faces for engagement by spanners.

4. A dental hand piece according to claim 1, wherein the outer diameter of said front, intermediate and rear sleeves is equal to the diameter of the bore of said external socket.

* * * * *